United States Patent [19]
Kuypers, Leonardus P. C. et al.

[11] Patent Number: 4,701,410
[45] Date of Patent: Oct. 20, 1987

[54] METHOD FOR THE IMMUNOCHEMICAL DETERMINATION OF HEPATITIS B CORE ANTIGENS

[75] Inventors: Kuypers, Leonardus P. C., Jv Oss; Gerrit Wolters, El Oss, both of Netherlands

[73] Assignee: Akzo N.V., Arnhem, Netherlands

[21] Appl. No.: 645,064

[22] Filed: Aug. 28, 1984

[30] Foreign Application Priority Data

Sep. 14, 1983 [NL] Netherlands ............... 8303169

[51] Int. Cl.⁴ ............... G01N 53/00; G01N 33/543
[52] U.S. Cl. ............... 435/7; 435/810; 436/518; 436/820
[58] Field of Search ............... 435/7, 810; 436/518, 436/820

[56] References Cited

U.S. PATENT DOCUMENTS

| | | | |
|---|---|---|---|
| 4,016,043 | 4/1977 | Schuurs et al. | 435/7 |
| 4,157,280 | 6/1979 | Halbert et al. | 435/7 |
| 4,241,175 | 12/1980 | Miller et al. | 435/7 |
| 4,317,810 | 3/1982 | Halbert et al. | 424/12 |
| 4,617,260 | 10/1986 | McAleer et al. | 436/820 X |

FOREIGN PATENT DOCUMENTS

| | | |
|---|---|---|
| 0012699 | 6/1980 | European Pat. Off. |
| 7610801 | 3/1977 | Netherlands |
| 2051357 | 1/1981 | United Kingdom |

OTHER PUBLICATIONS

Voller et al., *Immunoassays for the 80s*, pp. 367–369, University Park Press, Baltimore, 1983.
Chemical Abstracts, vol. 9, No. 1, 99:3880s, Jul. 4, 1983.
Biological Abstracts, vol. 69, No. 6, (U.S.), 38085, 1979.

*Primary Examiner*—Sidney Marantz
*Assistant Examiner*—Shawn P. Foley
*Attorney, Agent, or Firm*—William M. Blackstone

[57] ABSTRACT

The present invention concerns a method for detection of the core antigen of hepatitis B virus in a sample comprising a first incubation with carrier-bound antibodies directed against hepatitis B surface antigens and a second incubation with antibodies against the core antigen in the presence of a detergent.

Also claimed are test kits for carrying out this method and an immunochemical reagent comprising antibodies directed against the surface antigen and against the core antigen conjointly bound to a carrier.

21 Claims, No Drawings

METHOD FOR THE IMMUNOCHEMICAL DETERMINATION OF HEPATITIS B CORE ANTIGENS

The invention relates to a method for the qualitative and/or quantitative determination of hepatitis B core antigens and to test kits for use in this method.

In a viral hepatitis infection it is of importance, for making the correct diagnosis and for choosing the correct treatment method, to find out the nature of the pathogen, and where possible to determine the amount thereof which is present. Next to microbiological methods, immunochemical methods are most suitable for this purpose; these last-mentioned methods are in particular suitable for rapid routine determinations, which if desired can be carried out simply and in substantial numbers.

Using immunochemical methods, the antigens which are characteristic of the hepatitis virus in question can be detected qualitatively and quantitatively. Only the viral antigens which are present free in the sample to be investigated, or which are present on the surface of the virus, and thereby detected. Frequently, however, the information concerning the presence or concentration of such an antigen as yet gives no correct indication of the phase which the infection has reached. In particular, in hepatitis B virus (HBV) the complication arises that the presence or the concentration of the antigens thus detected is not an unambiguous indication of the presence or concentration of the intact infectious HB viruses. It is known that in an HBV infection in an advanced stage, and in chronic carriers of HBV, large quantities of the free virus coat- or surface-antigen (HBsAg) are present in the blood circulation, but, on the other hand, very few or no intact HB viruses (so-called Dane particles) are present. In an earlier phase of the HBV infection, on the other hand, substantial quantities of intact viruses are present. These intact viruses can be differentiated, by electron microscope methods, from HBsAg which is free and largely aggregated in various shapes, but such differentiation is not possible with the known immunochemical methods. Morphologically, the intact HB viruses are characterized by the presence of genetic material and other antigens (namely the core antigen (HBcAg)) within the coat of surface antigens. The coated HBcAg cannot be detected by the conventional immunochemical methods. A method whereby, through detection of HBcAg, the early stage of an infection can be revealed is, however, of the utmost importance.

A method has now been found whereby, surprisingly, an accurate and sensitive determination of HBcAg present in intact HBV particles in a sample to be investigated is feasible.

To this effect, the method according to the invention is characterized in that the sample is incubated with carrier-bound immunoglobulins directed against HBsAg, the carrier-bound and liquid phases are separated from one another, the carrier-bound phase is incubated with an agent which breaks the HBsAg coat and releases HBcAg and, simultaneously or subsequently, the solution obtained is incubated with immunoglobulins directed against HBcAg, after which any binding of HBcAg with immunoglobulins directed against it is determined, giving a qualitative and/or quantitative measure of HBcAg in the sample.

The possible binding of HBcAg to immunoglobulins directed against it can be detected by any method conventionally used for this purpose in immunochemistry. For example, it is possible to utilise an agglutination reaction or a so-called sandwich reaction.

If an agglutination reaction is used, the immunoglobulin directed against HBcAg is in general employed bound to particles. The possible presence of the antigen will then lead to agglutination of the particles, which can be detected qualitatively or quantitatively.

When, in the method according to the invention, the antigen is detected by means of a sandwich reaction, the antigen can be incubated with both a carrier-bound and a labelling-agent-bound immunoglobulin directed against HBcAg. The conjoint binding of both immunoglobulin derivatives to HBcAg will lead to the binding of labelling agent to the carrier, and the detection of carrier-bound or of free labelling agent gives a measure of the binding of immunoglobulin to antigen and hence of HBcAg present in the sample.

The carrier-bound immunoglobulins directed against HBcAg respectively can each be bound to different carriers and be brought simultaneously or independently of one another into contact with the test liquid, or can be conjointly bound to one and the same carrier. This last embodiment will in general give the method of determination which is simplest to carry out.

The invention also relates to a test kit which comprises at least some of the components required for carrying out the method according to the invention. Such a test kit then also comprises at least immunoglobulins directed against HBcAg as well as carrier-bound immunoglobulins directed against HBsAg. The immunoglobulins directed against HBcAg can, in the test kit, be bound to, for example, particles or to a carrier. This carrier can be the same as that on which the immunoglobulins directed against HBsAg are located or can be different therefrom. If desired, a test kit may also include auxiliary compounds for carrying out the determination according to the invention, such as compounds for the detection of the labelling agents, wash buffers and/or an agent which can break the coat of surface antigen.

As the carrier of immunoglobulins directed against HBsAg according to the invention, it is possible to use a body made of any material of any shape or size which provides the possibility of separating carrier-bound and non-carrier-bound phases from one another. The immunoglobulins may be bound directly or indirectly to the carrier. The binding to the carrier may take place by covalent bonds, ionic bonds or by means of hydrogen bridges, or may be based on, for example, van der Waals interactions. Examples of suitable carriers are test tubes, wells of microtitration plates or strips, rods, beads or discs produced from, for example, glass, plastics or naturally occurring substances.

Suitable agents for breaking the coat of HBsAg are, for example, detergents, such as sodium dodecyl sulphate, sodium dodecyl N-sarcosinate, cetyltrimethylammonium bromide, dodecylpyrimidinium chloride, palmitoyllysolecithin, dodecyl-N-betaine, polyoxyethylene-alcohols, polyoxyethylene-isoalcohols, polyoxyethylene-p-t-octylphenols, polyoxyethylene-nonylphenols, polyoxyethylene esters of fatty acids, polyoxyethylene sorbitol esters, sodium dodecylsulphonate, tetradecylammonium bromide and saponins. Amongst these, non-ionic detergents are preferred. Very suitable non-ionic detergents are the polyoxyethylene derivatives, including Brij, Triton, Nonidet P40 and Tween.

Particles which are suited for use with the invention are, for example, erythrocytes, latex beads, dyestuff sol particles or particles of metals or metal compounds.

All conventional labelling agents can be employed with the invention; they include enzymes, radioactive atoms or compounds, fluorescent substances, coloured compounds, dyestuff sols, sols or metals or metal compounds and the like.

The invention is further explained with reference to the following example.

EXAMPLE

Detection of HBcAg in serum

Two groups of sera in increasing dilutions were investigated; these sera were anti-HBc-positive and derived from HBsAg carriers, but in one serum Dane particles were detected under the electron microscope while in the other these particles were absent.

A. Reagents:

1. Coated microtitration plates.

The wells of polystyrene microtitration plates were coated on the inside with a mixture of immunoglobulins directed against HBsAg and against HBcAg by incubating this mixture in bicarbonate buffer of pH 9.0 in the wells for 24 hours at 20 °C. Thereafter the wells were washed with 0.15 mole/liter phosphate buffer of pH 7.2.

2. Conjugate.

A conjugate of immunoglobulins directed against HBcAg and horseradish peroxidase (HRP) was prepared according to the method of Nakane and Kawaoi (J. Histochem. Cytochem., 1974, 22, 1084–1091).

B. Procedure

The coated microtitration plates were incubated for 2 hours at 37 °C. with 0.1 ml of the serum to be investigated in each well, in a series of increasing dilutions in 0.15 mole/liter phosphate buffer of pH 7.2. Thereafter the wells were sucked empty, washed 3 times with 0.3 ml of 0.15 mole/liter phosphate buffer of pH 7.2, and sucked empty. Thereafter the wells were incubated for 2 hours at 37°C. with 0.1 ml of a solution of non-idet P40 in 0.15 mole/liter phosphate buffer of pH 7.2, washed 3 times with 0.3 ml of 0.15 mole/liter phosphate buffer of pH 7.2 and sucked empty.

Thereafter, 0.1 ml of the conjugate (A2), diluted in 0.15 mole/liter phosphate buffer of pH 7.2, was pipetted into each of the wells. After an incubation time of 1 hour at 37°C., the wells were sucked empty, washed 3 times with 0.3 ml of 0.15 mole/liter phosphate buffer of pH 7.2 and sucked empty. 0.1 ml of a mixture of 0.4 mg/ml of o-phenylenediamine and 0.4 mg/ml of urea peroxide in 0.15 mole/liter acetate buffer of pH 5.0 was then introduced into each of the wells. After 30 minutes' incubation, the reaction was stopped by adding 0.1 ml of 0.2mole/liter sulphuric acid solution.

The absorption of the solutions thus obtained was measured in a photometer at a wavelength of 492 nm.

C. Results

The results of the absorption measurements are reproduced in the table.

| Sera | Dilutions | | | | | |
|---|---|---|---|---|---|---|
| | Undiluted | ½ | ¼ | ⅛ | 1/16 | 1/32 |
| HBsAg positive and Dane particles | >2.000 | >2.000 | 1.150 | 0.638 | 0.401 | 0.276 |
| HBsAg positive and no Dane particles | 0.150 | 0.153 | 0.147 | 0.158 | 0.142 | 0.151 |
| HBsAg negative (control) | 0.149 | 0.143 | 0.150 | 0.161 | 0.149 | 0.153 |

It can be concluded that there is a positive correlation between the presence of Dane particles in serum and a concentration-dependent response in the test according to the invention.

We claim:

1. Method for the qualitative and/or quantitative immunochemical determination of hepatitis B core antigens (HBcAg), comprising incubating a liquid sample with carrier-bound immunoglobulins directed against hepatitis B surface antigens (HBsAg), separating the carrier-bound and liquid phases from one another, incubating the carrier-bound phase with an agent that breaks the HBsAg coat and releases HBcAg forming a solution with any HBcAg released, simultaneously with or subsequently to forming the solution incubating said solution with immunoglobulins directed against HBcAg, and determining the binding of HBcAg to immunoglobulins directed against HBcAg, giving a qualitative and/or quantitative measure of HBcAg in the sample.

2. Method according to claim 1, wherein the incubation with immunoglobulins directed against HBcAg is carried out with carrier-bound and labelling-agent-bound immunoglobulins, after which any binding of HBcAg to immunoglobulins is determined by measuring the carrier-bound or the free labelling agent.

3. Method according to claim 2, comprising employing a carrier to which the immunoglobulins directed against HBcAg and against HBsAg are conjointly bound.

4. Method according to claim 2 comprising employing an enzyme as the labelling agent.

5. Method according to claim 1, wherein the incubation with immunoglobulins directed against HBcAg is carried out with said immunoglobulins bound to particles.

6. Test kit for caryring out the determination according to claim 1, comprising carrier-bound immunoglobulins directed against HBsAg; immunoglobulins directed against HBcAg; and an agent effective for breaking down the HBsAg coat.

7. Test kit according to claim 6 further comprising which are bound immunoglobulins directd against HBsAg, labelling-agent-bound immunoglobulins directed against HBcAg.

8. Test kit according to claim 6 comprising immunoglobulins directed against HBsAg bound to a first carrier; immunoglobulins directed against HBcAg bound to a second carrier; and immunoglobulins directed against HBcAg, bound to a labelling agent.

9. Test kit according to claim 7 comprising an enzyme as labelling agent.

10. Test kit according to claim 9, comprising a substrate for the enzyme.

11. Test kit according to claim 6, comprising immunoglobulins directed against HBsAg, bound to a carrier;

and immunoglobulins directed against HBcAg, bound to particles.

12. Test kit according to claim 6, wherein the agent effective for breaking down the HBsAg coat comprises a detergent.

13. Test kit according to claim 12, comprising a non-ionic detergent.

14. Immunochemical reagent comprising antibodies directed against HBsAg and against HBcAg conjointly bound to a carrier.

15. Method according to claim 3, comprising employing an enzyme as the labelling agent.

16. Test kit according to claim 8, comprising an enzyme as labelling agent.

17. Test kit according to claim 7, wherein the agent effective for breaking down the HBsAg coat comprises a detergent.

18. Test kit according to claim 8, wherein the agent effective for breaking down the HBsAg coat comprises a detergent.

19. Test kit according to claim 9, wherein the agent effective for breaking down the HBsAg coat comprises a detergent.

20. Test kit according to claim 10, wherein the agent effective for breaking down the HBsAg coat comprises a detergent.

21. Test kit according to claim 11, wherein the agent effective for breaking down the HBsAg coat comprises a detergent.

* * * * *